(12) United States Patent
Maker

(10) Patent No.: US 9,757,457 B2
(45) Date of Patent: Sep. 12, 2017

(54) USE OF 2-DEOXY-D-GLUCOSE TO SENSITIZE CANCER CELLS TO AN AGENT THAT ACTIVATES THE EXTRINSIC APOPTOTIC PATHWAY

(71) Applicant: The Board of Trustees of the University of Illinois, Urbana, IL (US)

(72) Inventor: Ajay Maker, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 21 days.

(21) Appl. No.: 14/314,342

(22) Filed: Jun. 25, 2014

(65) Prior Publication Data

US 2014/0377274 A1 Dec. 25, 2014

Related U.S. Application Data

(60) Provisional application No. 61/839,121, filed on Jun. 25, 2013.

(51) Int. Cl.
*A61K 39/00* (2006.01)
*A61K 45/06* (2006.01)
*A61K 31/7004* (2006.01)
*A61K 31/555* (2006.01)

(52) U.S. Cl.
CPC ............ *A61K 45/06* (2013.01); *A61K 31/555* (2013.01); *A61K 31/7004* (2013.01)

(58) Field of Classification Search
CPC .......... A61K 39/39558; A61K 31/7004; A61K 45/06

See application file for complete search history.

(56) References Cited

U.S. PATENT DOCUMENTS

2011/0287001 A1* 11/2011 Holland ............... A61K 38/177
424/133.1

FOREIGN PATENT DOCUMENTS

WO    WO 2012/170640    * 12/2012

OTHER PUBLICATIONS

Maschek et al., Cancer Res. 64: 31-34, 2004.*
Munoz-Pinedo et al., JBC, 278: 12759-12768, 2003.*
Liu et al., Mol. Cancer, 2009, 8: pp. 1-17.*
Adrain, C. and Martin, S.J. "The Mitochondrial Apoptosome: a Killer Unleashed by the Cytochrome Seas" TRENDS in Biochemical Sciences 2001 26(6):390-397.
Ahmad et al. "Mitochondrial $O_2$ and $H_2O_2$ Mediate Glucose Deprivation-induced Cytotoxicity and Oxidative Stress in Human Cancer Cells" The Journal of Biological Chemistry 2005 280(6):4254-4263.
Cain et al. "The Apaf-1 Apoptosome: a Large Caspase-Activating Complex" Biochemie 2002 84:203-214.
Crane, R.K. and Sols, A. "The Non-Competitive Inhibition of Brain Hexokinase by Glucose-6-Phosphate and Related Compounds" The Journal of Biological Chemistry 1954 210:597-606.
Gambhir, S.S. "Molecular Imaging of Cancer with Positron Emission Tomography" Nature Reviews Cancer 2002 2:683-693.
Liu, H. et al. "2-Deoxy-D-Glucose Enhances TRAIL-Induced Apoptosis in Human Melanoma Cells through XBP-I-Mediated Up-Regulation of TRAIL-R2" Molecular Cancer 2009 8:122.
Liu, X. et al. "Dual Mechanisms for Glucose 6-Phosphate Inhibition of Human Brain Hexokinase" The Journal of Biological Chemistry 1999 274(44):31155-31159.
MacFarlane et al. "Glucose-a Sweet Way to Die" Cell Cycle 2012 11(21):3919-3925.
Maher et al. "Hypoxia-Inducible Factor-1 Confers Resistance to the Glycolytic Inhibitor 2-Deoxy-D-Glucose" Molecular Cancer Therapeutics 2007 6(2):732-741.
Qin et al. "2-Deoxyglucose Sensitizes Melanoma Cells to TRAIL-Induced Apoptosis which is Reduced by Mannose" Biochemical and Biophysical Research Communications 2010 401:293-299.
Simons et al. "Glucose Deprivation-Induced Metabolic Oxidative Street and Cancer Therapy" Journal of Cancer Research and Therapeutics 2009 5(Supplement 1)S2 doi:10.4103/0973-1482.55133.
Tomlinson et al. "Actual 10-Year Survival After Resection of Colorectal Liver Metastases Defines Cure" Journal of Clinical Oncology 2007 25(29):4575-4580.
Wallach et al. "Tumor Necrosis Factor Receptor and Fas Signaling Mechanisms" Annual Review of Immunology 1999 17:331-367.
Warburg, O. "On the Origin of Cancer Cells" Science 1956 123 (3191):309-314.
Wiering et al. "The Impact of Fluor-18-Deoxyglucose-Positron Emission Tomography in the Management of Colorectal Live Metastases" Cancer 2005 104(12):2658-2670.

* cited by examiner

*Primary Examiner* — Gyan Chandra
(74) *Attorney, Agent, or Firm* — Licata & Tyrrell P.C.

(57) ABSTRACT

Methods for sensitizing a solid tumor cell to an agent that activates the extrinsic apoptotic pathway and treating a solid tumor using a combination of 2-deoxy-D-glucose and an agent that activates the extrinsic apoptotic pathway are described.

4 Claims, 4 Drawing Sheets

USE OF 2-DEOXY-D-GLUCOSE TO SENSITIZE CANCER CELLS TO AN AGENT THAT ACTIVATES THE EXTRINSIC APOPTOTIC PATHWAY

INTRODUCTION

This application claims the benefit of priority of U.S. Provisional Application Nos. 61/839,121, filed Jun. 25, 2013, the content of which is incorporated herein by reference in its entirety.

BACKGROUND

It is well established that glucose uptake and metabolism is greater in cancer cells than normal cells (Warburg (1956) *Science* 123:309-14). Furthermore, whereas normal cells use glucose for maximal ATP production in aerobic environments, malignant cells favor anaerobic metabolism, even in oxygen-rich environments; an observation made over 50 years ago and termed the "Warburg effect." Malignant rapidly-growing cells typically have glycolytic rates many hundred times higher than cells of their normal tissues of origin. It is this distinguishing characteristic that has made it possible to identify malignant cells using 2-deoxy-2-fluoro-D-glucose (FDG) positron emission tomography (PET) scanning (Gambhir (2002) *Nat. Rev. Cancer* 2:683-93). Since FDG is a hexokinase substrate, it is taken up in a higher concentration in some types of cancer cells compared to normal cells.

Similar to FDG, but without the radiotag, 2-deoxy-D-glucose (2DG) is a hexokinase substrate that competes with glucose for uptake via glucose transporters and is selectively taken up at higher concentrations in malignant cells (Simons, et al. (2009) *J. Cancer Res. Ther.* 5 Suppl 1:S2-6). 2DG, once phosphorylated, is incapable of further metabolism in the pentose cycle and blocks the cycle before the generation of pyruvate. It acts as a glycolysis inhibitor by both competitively and allosterically inhibiting hexokinase and competitively inhibiting phosphoisomerase (Crane & Sols (1954) *J. Biol. Chem.* 210:597-606; Liu, et al. (1999) *J. Biol. Chem.* 274:31155-9; Maher, et al. (2007) *Mol. Cancer Ther.* 6:732-41). This thereby inhibits glucose metabolism and creates a state of glucose deprivation within the cell.

Cancer therapeutics predominantly act by inducing apoptosis via the intrinsic or extrinsic pathway. The intrinsic apoptotic pathway capitalizes on cytotoxic stress to form the apoptosome complex and is enhanced by radiation and certain chemotherapies (Adrain & Martin (2001) *Trends Biochem. Sci.* 26:390-7; Cain, et al. (2002) *Biochimie* 84:203-14). The extrinsic pathway is initiated by extracellular binding of tumor necrosis factor (TNF) members, including TNF-related apoptosis inducing ligand (TRAIL) to transmembrane death receptors (Wallach, et al. (1999) *Annu. Rev. Immunol.* 17:331-67). 2DG has been shown to increase sensitivity to TRAIL-induced apoptosis, even in TRAIL-resistant cancer cell lines (Liu, et al. (2009) *Mol. Cancer* 8:122; Qin, et al. (2010) *Biochem. Biophys. Res. Commun.* 401:293-9; MacFarlane, et al. (2012) *Cell Cycle* 11:3919-25).

Colon cancer is known to be a PET-avid malignancy, and the use of FDG-PET scanning has become critical in management of these patients, especially in identifying colorectal liver metastases (Wiering, et al. (2005) *Cancer* 104:2658-70). The current model of treating metastatic colorectal cancer involves a combination of surgery and chemotherapy. Surgery can only be performed on a minority of patients and the majority of these patients will experience tumor recurrence and die of disease (Tomlinson, et al. (2007) *J. Clin. Oncol.* 25:4575-80). Chemotherapy has inherent morbidity that prohibits use in patients with significant co-morbidities, and the best current regimens provides on average less than two-years of survival for patients with colorectal liver metastases. Therefore, new therapeutic approaches are needed.

SUMMARY OF THE INVENTION

The present invention includes methods for sensitizing a solid tumor cell to an agent that activates the extrinsic apoptotic pathway and treating a solid tumor using a combination of 2-deoxy-D-glucose and an agent that activates the extrinsic apoptotic pathway. In one embodiment, the solid tumor cancer is resistant to Tumor necrosis factor-Related Apoptosis Inducing Ligand-induced apoptosis (TRAIL). In other embodiments, the agent is TRAIL, oxaliplatin or an antibody (e.g., HGS-ETR1, HGS-ETR2, or a combination thereof) that binds to a cellular death receptor. In particular embodiments, the solid tumor cell is a colon, gastric or pancreatic tumor cells. A pharmaceutical composition containing 2-deoxy-D-glucose, an agent that activates the extrinsic apoptotic pathway, and at least one pharmaceutically acceptable carrier is also provided.

BRIEF DESCRIPTION OF THE DRAWINGS

FIG. 2A, HT-29 cells were treated with a general caspase inhibitor (Q-VD-OPh) and simultaneously treated with the indicated compounds. Apoptosis was assessed by Annexin V/PI staining. FIG. 2B, HT-29 cells were stably transfected with CrmA, DN-FADD plasmid constructs (a dominant-negative variant of FAS-associated via death domain protein) or an empty vector. These cell lines, as well as untransfected cells, were then treated with the indicated compounds and apoptosis was assessed by Annexin V/PI staining. n=3, * indicates p<0.05, ** indicates p<0.01, ns indicates p>0.05.

DETAILED DESCRIPTION OF THE INVENTION

Figure 1:
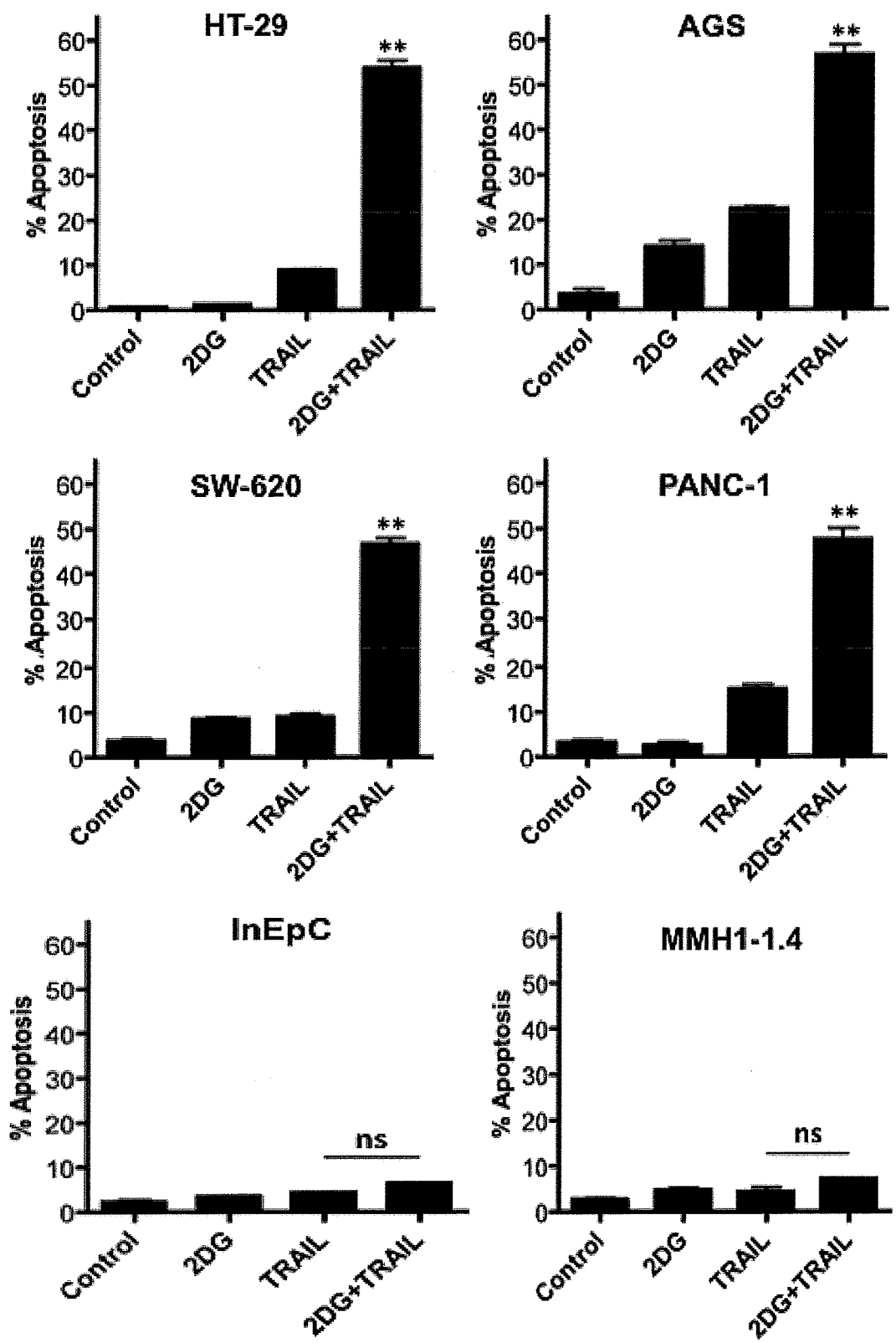
FIG. 1 shows that 2DG synergizes with TRAIL to induce cell death in TRAIL-resistant cancer cell lines (HT-29, AGS, SW-620 and PANC-1) but not normal human intestinal epithelial cells (InEpC cells) or liver cells (MMH1-1.4 cells). Apoptosis was detected by caspase-3 activation. n=3, ** indicates p<0.01, ns indicates p>0.05.

TRAIL induces apoptosis by activating the extrinsic pathway through death receptors DR4/5. It has been shown to induce apoptosis preferentially in cancer cell lines with little or no effect on normal tissue. As a result, TRAIL treatment has broad potential in cancer therapy, however, many tumors demonstrate both inherent and acquired resistance to TRAIL treatment.

Due to increased tumor cell glucose uptake and glycolysis, glycolytic inhibition with the glycolysis inhibitor 2DG has also been studied as an anti-cancer strategy. Though 2DG has been well-tolerated in clinical trials, its anti-tumor function appears limited to hypoxic conditions due to the ability of tumor cells to compensate for inhibited glycolysis with increased aerobic respiration. One of the observed effects of tumor cell 2DG treatment, however, is upregulation of death receptor surface expression.

It has now been found that glycolytic inhibition of cancer cells increases sensitivity of solid tumor cells to oxidative stress and death receptor-induced apoptosis, in particular death receptor 5-induced apoptosis. By way of illustration, the data presented herein indicates that 2DG synergizes with TRAIL treatment to dramatically increase apoptosis in TRAIL-resistant tumors. Moreover, 2DG administration upregulates both DR5 mRNA and total protein levels. In addition, treatment of cancer cells with 2DG and oxaliplatin is expected to enhance cytotoxicity in human cancer cells via metabolic oxidative stress and activation of the extrinsic apoptotic pathway. Therefore, the present invention provides a method for sensitizing a solid tumor cell to an agent that activates the extrinsic apoptotic pathway by contacting a solid tumor cell with an effective amount of 2-deoxy-D-glucose and an agent that induces, stimulates, or activates the extrinsic apoptotic pathway.

As is known in the art, 2-deoxy-D-glucose (2DG) is a non-metabolizable glucose analog having the following structure:

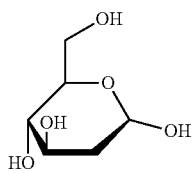

Inside a cell, 2DG is converted to phosphorylated 2-DG (2-DG-P) by hexokinase, the first and the rate-limiting enzyme in glycolysis. However, 2DG-P cannot be metabolized by the second enzyme in glycolysis, phosphoglucose isomerase (Parniak & Kalant (1985) *Can. J. Biochem. Cell Biol.* 63:333-40). This leads to trapping and accumulation of 2-DG-P, which competitively inhibits hexokinase at the rate-limiting step of glycolysis. Like 2DG, D-glucosone, 2-deoxy-D-aragino-hexose, and 2-amino-2-deoxy-D-glucose are also phosphorylated by hexokinase (Hudson (1945) *Advances Carbohyd. Chem.* 1:1; Johnstone & Mitchell (1953) *Biochem. J.* 55:xvii; Brown (1951) *Biochim. et Biophys. Acta* 7:487; Grant & Long (1952) *Biochem. J.* 50; Crane & Sols (1953) *J. Biol. Chem.* 203:273; Harpur & Quastel (1949) *Nature* 164:693; see also *Advances in Carbohydrate Chemistry* (1956) Vol. 11, Academic Press). D-glucosone has been shown to slowly dissociate from the enzyme (Fleury & Courtois (1946) *Compt. Rend.* 223:633) and assume "pseudo-irreversible" inhibition (Ackermann & Potter (1948) *Proc. Soc. Exptl. Biol. Med.* 72:1). In addition, D-glucosamine, iso-glucosamine, and 5-thioglucose have also been found to inhibit hexokinase activity (Machado de Domenech & Sols (1980) *FEBS Lett.* 119:174-176; Fernandez, et al. (1985) *IJ. Gen. Microbiol.* 131:2705; Sols et al. (1958) *Biochem. Biophys. Acta* 30:92-101). Therefore, in addition to 2DG, one or more of the above-reference hexokinase inhibitors can be used in accordance with the present invention.

A solid tumor cell refers to a malignancy that forms a discrete tumor mass and includes, e.g., cancer of the lung, pancreas, brain, breast, prostate, colorectum, stomach, ovary, bladder, testicle, esophagus, liver, kidney and skin (i.e., melanoma). By comparison, lymphoproliferative malignancies such as leukemia, myeloma or lymphoma, diffusely infiltrate a tissue without forming a mass and are therefore not considered solid tumors. In particular embodiment, the solid tumor is a colon, gastric or pancreatic tumor.

As demonstrated herein, 2DG was particularly effective in the sensitization of tumor cells, which were resistant to TRAIL-induced apoptosis. Accordingly, in certain embodiments, the solid tumor being treated exhibits resistance to TRAIL-induced apoptosis. A tumor that is resistant to TRAIL-induced apoptosis refers to cancers that have become resistant to treatment with TRAIL and no longer undergo apoptosis upon treatment with TRAIL.

Sensitization or sensitizing a solid tumor to an agent that activates the extrinsic apoptotic pathway refers to an improved or enhanced response of a tumor or cancer cell to a cancer therapy. Alternatively stated, sensitized cancer cells respond better to cancer therapy (are inhibited or killed faster or more often) than non-sensitized cells, as follows: Control samples (untreated with sensitizing agents) are assigned a relative cancer therapy response value of 100%. Sensitization is achieved when the cancer therapy response value relative to the control is about 110% or 120%, preferably 200%, more preferably 500-1000% or more, i.e., at least about 10% more cells are killed or inhibited, or the cells are killed or inhibited at least about 10% faster. Cancer therapy response value refers to the amount of killing or inhibition of a cancer cell, or the speed of killing or inhibition of a cancer cell when it is treated with a cancer therapy. Some compounds are useful both as therapeutic reagents and as sensitizing reagents. Often, a lower dose (i.e., lower than the conventional therapeutic dose) or sub-toxic dose of such a reagent can be used to sensitize a cell. Often, when a cell is sensitized, a lower dose of the chemotherapeutic reagent can be used to achieve the same therapeutic effect as with a cell that has not been sensitized.

The exact dose of 2DG and/or agent that activates the extrinsic apoptotic pathway will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

An agent that activates the extrinsic apoptotic pathway is an agent that modulates the expression or activity of a molecule that is a component or mediator of the extrinsic pathway of apoptosis. One set of mediators implicated in apoptosis include caspases, cysteine proteases that cleave their substrates specifically at aspartate residues. Caspases convey the apoptotic signal in a proteolytic cascade, with caspases cleaving and activating other caspases which subsequently degrade a number of target death proteins, such as poly (ADP-ribose) polymerase, eventually resulting in cell death. If one or more steps in this cascade are inhibited in tumor cells, these cells fail to undergo apoptosis and, thus, continue to grow. Activation of caspases can be initiated from different entry points, for example, at the plasma membrane upon ligation of death receptor (receptor pathway). Stimulation of death receptors of the tumor necrosis factor (TNF) receptor superfamily such as CD95 (APO-1/Fas) or TRAIL receptors 1 and 2 results in activation of the initiator caspase-8 which can propagate the apoptosis signal by direct cleavage of downstream effector caspases such as caspase-3 (Walczak & Krammer (2000) *Exp. Cell Res.* 256:58-66).

In some embodiments, an agent that activates the extrinsic apoptotic pathway refers to substances that induce apoptosis by binding to death receptors, e.g., ligands. Preferred ligands of death receptors are tumor necrosis factor α (TNF-α), tumor necrosis factor (TNF-β, lymphotoxin α), lymphotoxin β (LT-β), TRAIL (Apo2L), CD95 (Fas, APO-I) ligand, TRAMP (DR3, Apo-3) ligand, DR4 ligand, DR6 ligand as well as fragments and derivatives of said ligands.

A preferred ligand that activates the extrinsic apoptotic pathway is TRAIL (Apo2L). "TRAIL" (TNF-related apoptosis-inducing ligand) refers to a cytokine that is produced and secreted by most normal tissues cells. The full-length human TRAIL polypeptide is a 281 amino acid long, Type II transmembrane protein. See UniProtKB/Swiss-Prot Accession No. P50591. TRAIL causes apoptosis by binding to the death receptors DR4 and DR5. The terms "Apo2L/TRAIL," "Apo2L," "Apo-2 ligand" and "TRAIL" are used herein to refer to the TRAIL polypeptide sequence as well as biologically active fragments, deletional, insertional, or substitutional variants thereof. In some embodiments, the fragments or variants are biologically active and have at least about 80% amino acid sequence identity, more preferably at least about 90% sequence identity, and even more preferably, at least 95%, 96%, 97%, 98%, or 99% sequence identity with the human TRAIL sequence. This definition encompasses substitutional variants of TRAIL in which at least one of its native amino acids are substituted by an alanine residue. These substitutional variants include those identified, for example, as "D203A," "D218A" and "D269A." This nomenclature is used to identify Apo2L/TRAIL variants wherein the aspartic acid residues at positions 203, 218, and/or 269 are substituted by alanine residues. See U.S. Pat. No. 7,741,282. Optionally, the TRAIL variants may include one or more of the alanine substitutions, which are recited in Table I of WO 01/00832. Substitutional variants include one or more of the residue substitutions identified in Table I of WO 01/00832. The definition also encompasses a native sequence of TRAIL isolated from a TRAIL source or prepared by recombinant or synthetic methods. The TRAIL of the invention includes the polypeptides referred to as Apo2L/TRAIL or TRAIL disclosed in WO 97/01633 and WO 97/25428. In some embodiments, the TRAIL of the invention is Superkiller-TRAIL, as described by Wang, et al. ((2004) *Cancer Cell* 5:501). The terms "Apo2L/TRAIL" or "Apo2L" are also used to refer generally to forms of TRAIL that include monomer, dimer or trimer forms of the polypeptide. The person skilled in the art knows that the aforementioned proteins may be produced using standard techniques for the production of recombinant proteins. Alternatively, recombinant Apo2L/TRAIL is commercially available, for example from Prospec (East Brunswick, N.J.).

In other embodiments, an agent that activates the extrinsic apoptotic pathway refers to antibodies directed against cellular death receptors. In particular embodiments, the antibody is a monoclonal antibody that binds to cellular death receptors and has been shown to induce cell death in different types of tumor cells. Examples of such antibodies include, but are not limited to, anti-CD95 antibody, anti-TRAIL-R1 (D4) antibody, anti-TRAIL-R2 (D5) antibody, anti-DR6 antibody, anti TNF-R1/2 antibody and anti-TRAMP (DR3) antibody as well as fragments or derivatives thereof. In some embodiments, the antibody is an anti-TRAIL-R1 (D4) antibody. An exemplary anti-TRAIL-R1 (D4) antibody includes, but is not limited to, mapatumumab (HGS-ETR1). Mapatumumab is an agonistic monoclonal antibody to TRAIL-R1 with apoptosis promoting and potential antitumor activities. Mapatumumab selectively binds to and activates the TRAIL cell receptor, thereby inducing apoptosis and reducing tumor growth. In another embodiment, the antibody is an anti-TRAIL-R2 (D5) antibody. An exemplary anti-TRAIL-R2 (D5) antibody includes, but is not limited to, lexatumumab (HGS-ETR2). Lexatumumab is a fully human monoclonal agonistic antibody directed against TRAIL-R2 with potential antitumor activity. Mimicking the natural ligand TRAIL, lexatumumab binds to and activates TRAIL-R2, which may trigger apoptosis in and inhibit the growth of TRAIL-R2-expressing tumor cells. Additional monoclonal antibodies that bind cellular death receptors include conatumumab (AMG655), dulanermin (AMG 951, APO2L/TRAIL, PRO1762, RG3639, rhApo2L/TRAIL), tigatuzumab (CS1008), TRAIL R (DR4-Specific Altrimer, Anaphore), HGS TR2J, LBY135, drozitumab (PR085780, apomab), SL231, SM164 with TRAIL R2, TAS266, and the like.

In still other embodiments, an agent that activates the extrinsic apoptotic pathway refers to a chemotherapeutic agent that has been shown to activate the extrinsic apoptotic pathway. For example, treatment with DNA-damaging agents such as doxorubicin, etoposide, cisplatin or bleomycin have been shown to trigger an increase in CD95L expression, which stimulates the receptor pathway in an autocrine or paracrine manner by binding to its receptor CD95 (Friesen, et al. (1996) *Nat. Med.* 2:574-577; Fulda, et al. (1997) *Cancer Res.* 57:3823-3829; Fulda, et al. (1998) *Int. J. Cancer* 76:105-114; Houghton, et al. (1997) *Proc. Natl. Acad. Sci. USA* 94:8144-8149; Muller, et al. (1997) *J. Clin. Invest.* 99:403-413). The CD95 receptor/ligand system has also been implicated in thymine-less death in colon carcinoma cells following treatment with 5-fluorouracil (Houghton, et al. (1997) supra). Furthermore, upregulation of FADD and procaspase-8 has been found upon treatment with doxorubicin, cisplatin or mitomycin C in colon carcinoma cells (Micheau, et al. (1999) *Biophys. Res. Commun.* 256:603-611). Moreover, oxaliplatin has been shown to increase caspase-8 activity and increase Bid expression in colorectal cancer cells (DiCesare, et al. (2013) *Free Radic. Biol. Med.* 61C:143-150). Accordingly, in certain embodiments, the agent that activates the extrinsic apoptotic pathway is oxaliplatin.

Sensitizing a solid tumor cell to an agent that activates the extrinsic apoptotic pathway is particularly useful in the treatment of cancer. Accordingly, the present invention also includes a method for treating a solid tumor by administering to a subject in need of treatment an effective amount of 2-deoxy-D-glucose and an agent that activates the extrinsic apoptotic pathway. The term "treating" or "treatment" as used herein covers the treatment of a disease or disorder described herein, in a subject, preferably a human, and includes inhibiting a disease or disorder, i.e., arresting its development; relieving a disease or disorder, i.e., causing regression of the disorder; slowing progression of the disorder; and/or inhibiting, relieving, or slowing progression of one or more symptoms of the disease or disorder. Said treating also includes an entire restoration of the health with respect to cancers referred to herein. The term "treatment," in relation to the treatment of cancer, is to be understood as embracing both symptomatic and prophylactic modes, that is the immediate treatment, e.g., of acute cancer (symptomatic treatment) as well as advance treatment to prevent, ameliorate or restrict long term symptomatology (prophylactic treatment). The term "treatment" in relation to such cancers is to be interpreted accordingly as including both symptomatic and prophylactic treatment, e.g., symptomatic treatment to reduce the tumor size, preferably to kill all tumor cells, and prophylactic treatment to inhibit the formation of new cancer cells. It is to be understood that treating as used in accordance with the present invention may not be effective in all subjects to be treated. However, the term shall require that a statistically significant portion of subjects suffering from a cancer referred to herein can be successfully treated. Whether a portion is statistically significant can be determined without further ado by the person skilled in the art using various well-known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 60%, at least 70%, at least 80%, or at least 90% of the subjects of a given cohort or population.

"Subject" refers to a warm-blooded animal such as a mammal, preferably a human, or a human child, which is afflicted with, or has the potential to be afflicted with one or more cancers described herein.

The combined use of 2DG and at least one agent that activates the extrinsic apoptotic pathway is especially preferred in cancers that respond poorly to conventional chemotherapy alone. Preferably, cells of such cancers display resistance against one or more of the agents used. Resistance means that the cells can survive or even proliferate further in a subject even though the subject is treated with the usual amounts of the chemotherapeutic agent or agents in question. Advantageously, the combination of 2DG and at least one agent that activates the extrinsic apoptotic pathway can be used to increase the efficacy of the currently used chemotherapeutic agents. It has been found that the combination of 2DG with TRAIL synergistically enhances the effects of the chemotherapeutic agent.

Given the activity of the combination therapy, the agent that activates the extrinsic apoptotic pathway can be applied in dosages that are currently used in conventional treatment protocols. This approach promises to increase the effect of conventional treatment protocols for chemotherapy, i.e., the rate of successfully treated patients can be expected to rise. Furthermore, patients with tumors that are resistant to the currently used dosages of agents may profit from the combination therapy because 2DG increases the effect of the currently used agents.

Also possible is a second approach, wherein the agent that activates the extrinsic apoptotic pathway is at a decreased dosage and still retains its efficacy due to the combination with 2DG. Treatment protocols that require reduced dosages of the agent that activates the extrinsic apoptotic pathway have the potential to reduce the undesired and often severe side effects of chemotherapy. Thus, a combination therapy with 2DG and decreased dosages of an agent that activates the extrinsic apoptotic pathway may enable the treatment of patients in bad general condition that are not eligible for conventional chemotherapeutic treatment regimens due to the expected side effects. For some types of cancer that can already be cured chemotherapy in a majority of patients, the combination treatment of the present invention promises to reduce the required dosage of chemotherapeutic agents. Thus, in these cases a combination therapy may improve the quality of life for the patients without compromising the success of the treatment.

The combination therapy of the present invention can be administered simultaneously in a combined preparation or administered simultaneously or sequentially as separate formulations. Many of the agents that activate the extrinsic apoptotic pathway are known in the art and already provided as pharmaceutical compositions. As such, the 2DG can be admixed into these pharmaceutical compositions. However, when prepared as a separate formulation, preferably the 2DG is in admixture with at least one pharmaceutically acceptable carrier. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, phosphate buffer solutions; non-toxic, compatible lubricants such as sodium lauryl sulfate and magnesium stearate; as well as coloring agents, releasing agents, coating agents, sweetening, flavoring and perfuming agents. Preservatives and antioxidants can also be present in the composition, according to the judgment of the formulator.

The pharmaceutical composition(s) of this invention may be administered to humans and other animals orally, rectally, parenterally, intracisternally, intravaginally, intraperitoneally, topically (as by powders, ointments, drops or transdermal patch), bucally, or as an oral or nasal spray. The term "parenteral," as used herein, refers to modes of administration which include intravenous, intramuscular, intraperitoneal, intrasternal, subcutaneous and intraarticular injection and infusion. Dosage forms for topical or transdermal administration of 2DG include ointments, pastes, creams, lotions, gels, plasters, cataplasms, powders, solutions, sprays, inhalants or patches. The active component, i.e., the 2DG, is admixed under sterile conditions with a pharmaceutically acceptable carrier and any needed preservatives or buffers as may be required. The ointments, pastes, creams and gels may contain, in addition to 2DG, excipients such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to 2DG, excipients such as lactose, talc, silicic acid, aluminum hydroxide, calcium silicates and polyamide powder, or mixtures of these substances. Sprays can additionally contain customary propellants such as chlorofluorohydrocarbons. For nasal administration, 2DG will suitably be administered in liquid or powdered form from a nasal applicator. Forms suitable for ophthalmic use will include lotions, tinctures, gels, ointment and ophthalmic inserts, again as known in the art. For rectal administration, i.e., for topical therapy of the colon, 2DG may be administered in suppository or enema form, in particular in solution, e.g., in vegetable oil or like oily system for use as a retention enema.

In general, the pharmaceutical composition(s) of this invention will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compositions of the disclosure for a given disease.

For purposes of the disclosure, generally a therapeutic amount will be in the range of about 0.01 mg/kg to about 250 mg/kg body weight, more preferably about 0.1 mg/kg to about 10 mg/kg, in at least one dose. In larger mammals the indicated daily dosage can be from about 1 mg to 300 mg, one or more times per day, more preferably in the range of about 10 mg to 200 mg. The subject can be administered as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the active ingredient.

The following non-limiting examples are provided to further illustrate the present invention.

EXAMPLE 1

Response of Cancer Cell Lines to TRAIL and 2DG

TRAIL has been shown to induce apoptosis preferentially in cancer cell lines with little or no effect on normal tissue (Ashkenazi, et al. (1999) *J. Clin. Invest.* 104:155-62; Walczak, et al. (1999) *Nat. Med.* 5:157-63). While this makes TRAIL a promising anti-cancer therapy, there are numerous examples of both inherent and acquired resistance to TRAIL treatment. In a phase I trial of TRAIL in human cancer patients with various tumor histologies, TRAIL was well-tolerated, however, none of the patients with colorectal cancer had an objective tumor response (Herbst, et al. (2010) *J. Clin. Oncol.* 28:2839-46). It was posited that this may have been due to either inherent or acquired TRAIL resistance. Therefore, a panel of well-established human colorectal tumor cell lines (HT-29, COLO-205 and SW-620) was analyzed to determine TRAIL sensitivity. Varying levels of TRAIL-induced apoptosis was observed, with the cell line HT-29 demonstrating resistance to TRAIL at even maximal doses (FIG. 1). Therefore, this human cell line was selected for use as a model for in vitro experiments.

To assess the effect of 2DG on HT29 cells, HT29 cells were treated with increasing doses (0-50 mM) of 2DG in vitro. This analysis indicated that there was no difference in tumor cell apoptosis (≤5%) at any of the doses as measured by Annexin V staining utilizing flow cytometry.

To assess the effect of TRAIL on colon (HT29, COLO-205, SW-620), gastric (AGS) and pancreatic (PANC-1) cancer cell lines, cells were treated with increasing doses (0, 6.25, 12.5, 25, 50 and 100 ng/mL) of TRAIL in vitro. This analysis indicated that there was no difference in tumor cell apoptosis (≤12%) at any of the doses as measured by Annexin V staining utilizing flow cytometry.

Using optimized doses of 2DG and TRAIL (10 mM 2DG and 50 ng/mL of TRAIL), the combination of 2DG and TRAIL was found to significantly increase tumor cell apoptosis in HT29 and SW-620 colon cancer cells, the AGS gastric cancer cell line and the PANC-1 pancreatic cancer cell line (FIG. 1). This data indicates that the combination of TRAIL and 2DG finds application in a generalized method to treat multiple types of solid tumors.

Figure 2A:
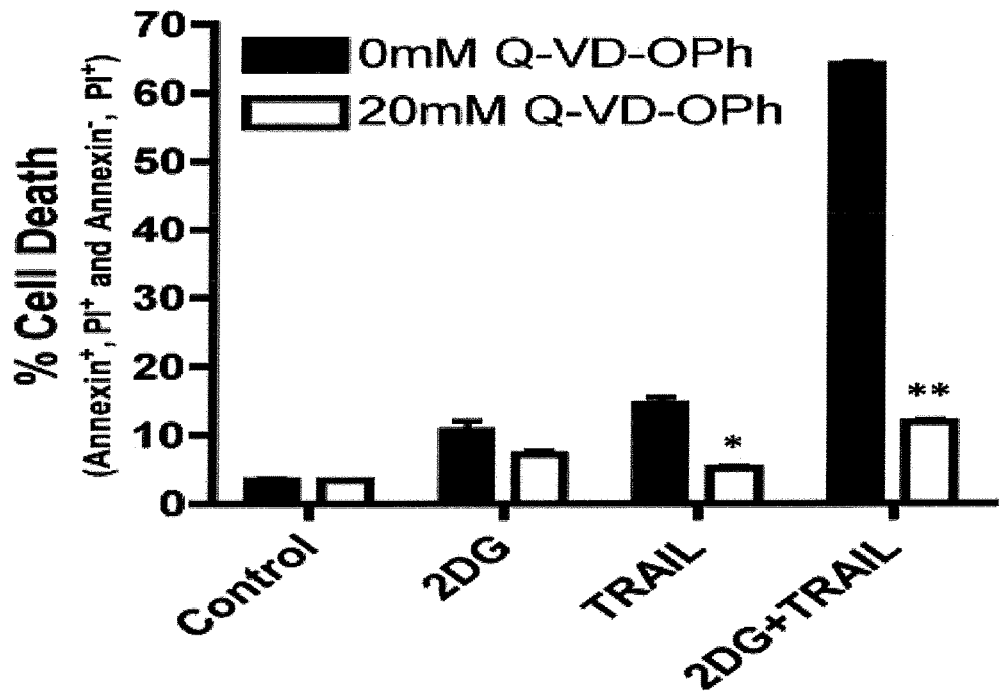
FIGS. 2A and 2B show that blockade of the extrinsic apoptotic pathway abrogates 2DG and TRAIL synergy.
Figure 2B:
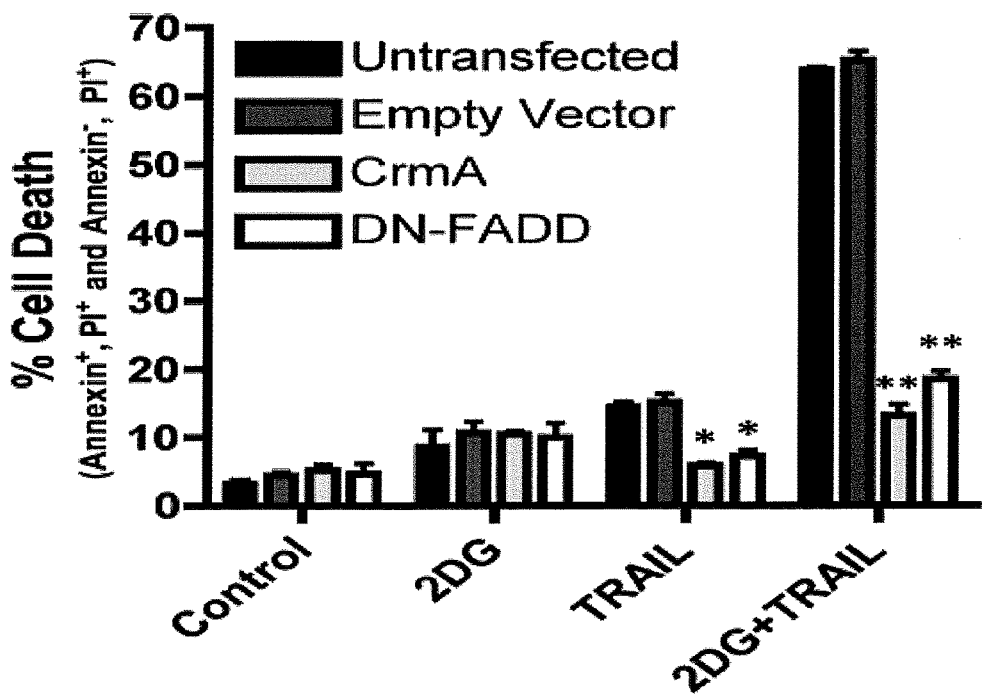

To determine the mechanism of apoptosis, HT-29 and SW-620 cells were treated every 6 hours with 2DG, TRAIL or 2DG and TRAIL. This analysis showed only robust caspase-8 activation (as indicated by p18 and p10 cleavage products) and caspase-3 activation (as indicated by p19 and p17 cleavage products) with the combination therapy. HT-29 cells were also fractionated into cytoplasmic and membrane-heavy fractions, with COXIV as a marker of the membrane heavy fraction and beta actin as a loading control. Truncated Bid (tBid) was only found in the membrane heavy faction of the 2DG and TRAIL treated cells. To confirm that the combination treatment enhanced activation of the extrinsic apoptotic pathway, cells were treated with a general caspase inhibitor (Q-VD-OPh) or inhibitors of caspase 8 (CrmA and a dominant-negative variant of the FADD) and simultaneously treated with 2DG, TRAIL or 2DG and TRAIL. This analysis indicated that blockade of the extrinsic pathway inhibited the anti-tumor effect of the combination treatment (FIGS. 2A and 2B).

EXAMPLE 2

Effect of 2DG Treatment on Death Receptor Expression

TRAIL mediates its effects by binding to cell surface death receptors 4 and 5 (DR4, DR5). This initiates the extrinsic apoptosis pathway ultimately resulting in cell death. Therefore, it was determined whether 2DG primes tumor cells to TRAIL by altering DR expression in HT29 cells. This analysis indicated that DR5 mRNA and total protein levels were upregulated on colon cancer cells after treatment with 2DG. By comparison, DR4 levels were unchanged by 2DG treatment. In addition, increased surface expression of DR5 correlated with TRAIL sensitivity over time. However, increased DR5 expression was not the primary determinant of 2DG+TRAIL sensitivity because 2DG+TRAIL-treated cells still underwent apoptosis in the presence of shRNA molecules that specifically decreased the expression of DR5.

EXAMPLE 3

Mechanism of 2DG Sensitization to TRAIL-Induced Apoptosis

Figure 3:
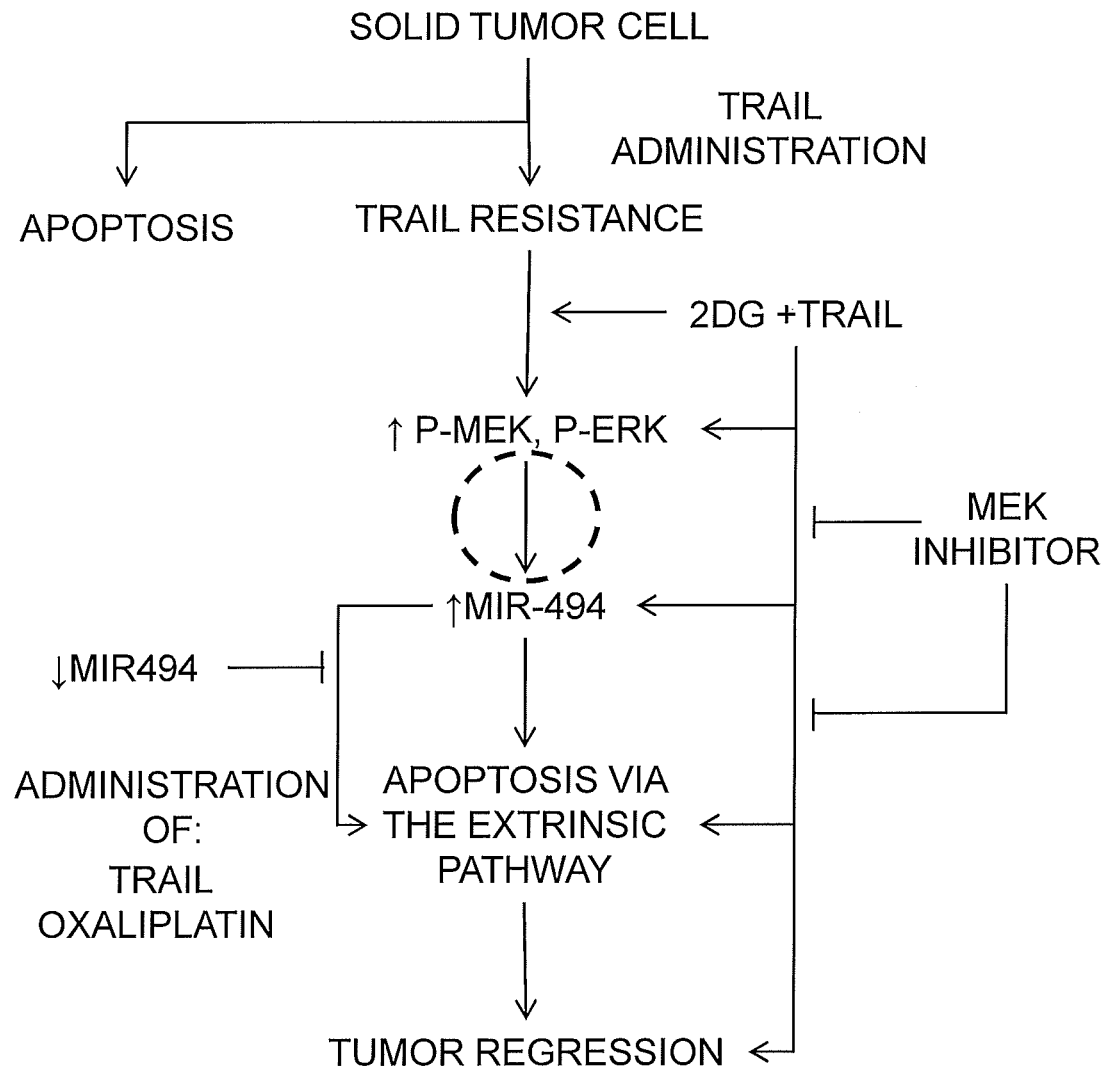
FIG. 3 illustrates a mechanism of TRAIL-mediated apoptosis and tumor regression.

A number of microRNA (miRNA) molecules have been implicated in TRAIL-induced cell death. Accordingly, analysis of 800 miRNAs was carried out to determine whether specific miRNAs were upregulated by 2DG+TRAIL. Four miRNAs, miR-494, miR-1246, miR-4488 and miR4516, were found to be highly up-regulated in the 2DG+TRAIL treatment group relative to 2DG or TRAIL alone. To determine the role of these miRNA molecules, the expression of each miRNA was modulated and the effect on apoptosis was analyzed. The results of this analysis indicated that inhibition of miR-494 reduced 2DG+TRAIL-induced apoptosis, whereas overexpression of miR-494 enhanced TRAIL-induced apoptosis. Therefore, 2DG or a similar glucose analog, could also be used in combination with an agent that modulates the expression of one or more of these miRNAs or members of the pathway regulated by these miRNA, e.g., MEK or Erk pathway (Romano, et al. (2012) *Proc. Natl. Acad. Sci. USA* 109:16570-5), in the treatment of cancer (FIG. 3).

EXAMPLE 4

In Vivo Effect of Tumor Cell Exposure to 2DG and TRAIL

Concomitant with the in vitro studies, in vivo studies were conducted to determine the role of 2DG sensitization of cancer cells to TRAIL in a xenograft model. Colon cancer cells ($5 \times 10^6$ cells) were injected s.c. into athymic mice and the tumor formation was allowed to occur for one week. Subsequently, established tumors were treated for consecutive days with 0.5 mg/kg 2DG/g body weight (i.p.) and 100 µg TRAIL (i.t.) thereafter.

Figure 4:
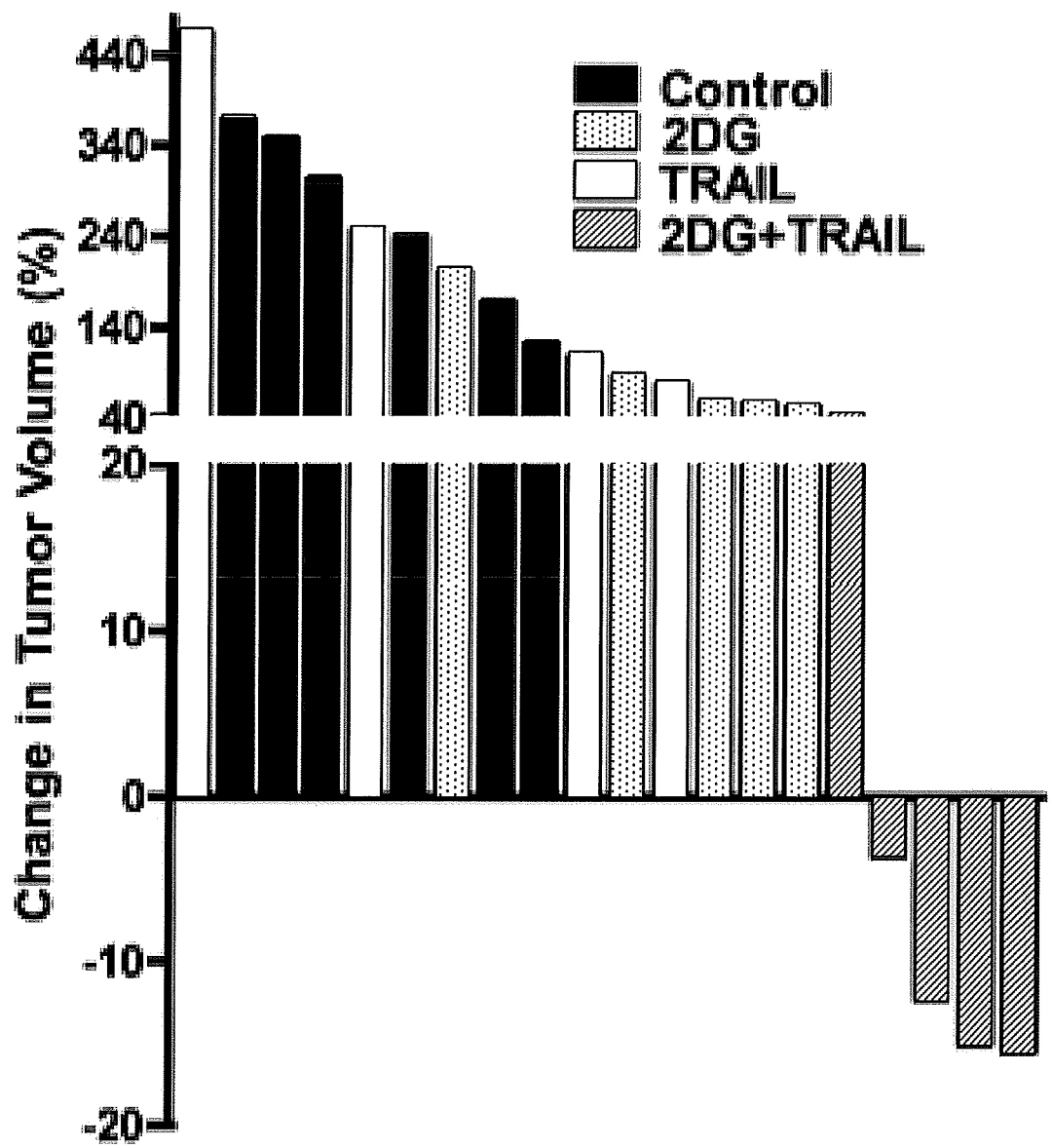
FIG. 4 provides data showing that 2DG and TRAIL cause regression of established solid tumors in vivo. Shown is a waterfall plot where each bar represents a single mouse of the indicated treatment group. The data represents the per cent change in tumor volume after five days of treatment relative to tumor volume on day 0.

A bicistronic lentiviral vector was also used to deliver both luciferase and green fluorescent protein (GFP) to colon cancer cells thereby allowing in vivo non-invasive bioluminescent tumor imaging via the Xenogen IVIS system. This analysis of the tumors indicated that the 2DG and TRAIL combination resulted in the regression of established human colorectal cancer cell tumors in the murine model (FIG. 4), thereby demonstrating the use of these agents in the treatment of cancer.

EXAMPLE 5

Combination of 2DG Treatment With Promoters of Oxidative Stress

Several studies have demonstrated that glucose deprivation induces oxidative stress in human cancer cells (Simons, et al. (2009) *J. Cancer Res. Ther.* 5 Suppl 1:S2-6; Simons, et al. (2007) *Cancer Res.* 67:3364-70; Spitz, et al. (2000) *Ann. NY Acad. Sci.* 899:349-62). Furthermore, increased pro-oxidant production and dysregulation of thiol metabolism have also been noted in cancer cells during glucose deprivation or when treated with 2DG (Ahmad, et al. (2005) *J. Biol. Chem.* 280:4254-63). 2DG-induced cytotoxicity has also been shown to be inhibited by the antioxidant N-acetylcysteine (Lin, et al. (2003) *Cancer Res.* 63:3413-7). Therefore, it is posited that glucose deprivation via 2DG treatment is associated with increased oxidative stress within the tumor cell.

Oxaliplatin is an effective antitumor agent and is a first-line standard of care chemotherapeutic when combined with 5-FU and leucovorin for locally advanced or metastatic colon cancers. Tumor cell death is believed to be secondary to oxaliplatin-DNA adducts that inhibit DNA replication and transcription, though its cytotoxicity may also be related to the inhibition of thioredoxin reductase activity, which protects cells from oxidative stress (Witte, et al. (2005) *Free Radic. Biol. Med.* 39:696-703). Further, in contrast to normal astrocytes cells, where oxaliplatin activates the intrinsic apoptotic pathway, oxaliplatin has been shown to increase caspase-8 activity (one of the main effectors of the extrinsic apoptotic pathway) and increase Bid expression (a protein activated by caspase-8) in colorectal cancer cells (DiCesare, et al. (2013) *Free Radic. Biol. Med.* 61C:143-150).

Modulation of intracellular thiol levels has been shown to influence cytotoxicity of other platinum-based chemotherapies, and the combination of 2DG with cisplatin resulted in increased cytotoxicity of head and neck tumor cells (Simons, et al. (2007) *Cancer Res.* 67:3364-70).

Therefore, it is believed that treatment of human colon cancer cells with 2DG and oxaliplatin will modulate total glutathione content (i.e., reduced glutathione (GSH)+glutathione disulfide (GSSG)), cause an increase in percentage of GSSG, and enhance cytotoxicity. It is further expected that treatment with the thiol antioxidant N-acetylcysteine can abrogate this cytotoxicity, whereas treatment with the GSH-depleting agent L-buthionine-[S,R]-sulfoximine (BSO) will enhance cytotoxicity. The combination of 2DG and oxaliplatin is expected to enhance cytotoxicity in human colorectal cancer cells via metabolic oxidative stress. Further, given the activity of TRAIL, it is believed that standard care oxaliplatin chemotherapy can be enhanced by addition of the combination of 2DG and TRAIL treatment.

What is claimed is:

1. A method for sensitizing a Tumor necrosis factor-Related Apoptosis Inducing Ligand (TRAIL)-resistant colon, gastric or pancreatic solid tumor cell to an agent that activates the extrinsic apoptotic pathway comprising contacting a TRAIL-resistant colon, gastric or pancreatic solid tumor cell with a composition consisting of an effective amount of 2-deoxy-D-glucose and an antibody that activates the extrinsic apoptotic pathway by binding to cellular death receptor 3, 4, 5 or 6 thereby sensitizing the solid tumor cell to an agent that activates the extrinsic apoptotic pathway, wherein the antibody is HGS-ETR1, HGS-ETR2, or a combination thereof.

2. A pharmaceutical composition for treating a Tumor necrosis factor-Related Apoptosis Inducing Ligand-resistant colon, gastric or pancreatic cancer consisting of 2-deoxy-D-glucose, an antibody that activates the extrinsic apoptotic pathway by binding to cellular death receptor 3, 4, 5 or 6, and at least one pharmaceutically acceptable carrier, wherein the antibody is HGS-ETR1, HGS-ETR2, or a combination thereof.

3. A method for treating a Tumor necrosis factor-Related Apoptosis Inducing Ligand (TRAIL)-resistant colon, gastric or pancreatic solid tumor comprising administering to a subject in need of treatment the pharmaceutical composition of claim 2, thereby treating the subject's TRAIL-resistant colon, gastric or pancreatic solid tumor, wherein the antibody is HGS-ETR1, HGS-ETR2, or a combination thereof.

4. A suppository or enema for treating a Tumor necrosis factor-Related Apoptosis Inducing Ligand-resistant colon cancer consisting of 2-deoxy-D-glucose, an agent that activates the extrinsic apoptotic pathway by binding to a death receptor, and at least one pharmaceutically acceptable carrier, wherein the antibody is HGS-ETR1, HGS-ETR2, or a combination thereof.

* * * * *